United States Patent [19]

Huber et al.

[11] Patent Number: 5,468,490
[45] Date of Patent: Nov. 21, 1995

[54] LIPIDIC FURANS USEFUL FOR SKIN THERAPEUTICS

[75] Inventors: S. Richard Huber, Camarillo, Calif.; David F. Counts, Coram, N.Y.

[73] Assignee: Conkle & Olesten, Los Angeles, Calif.

[21] Appl. No.: 142,808

[22] Filed: Oct. 25, 1993

[51] Int. Cl.$^6$ .................................................. A61K 31/34
[52] U.S. Cl. .................................... 424/78.03; 514/461
[58] Field of Search ..................... 514/461; 424/78.03

[56] References Cited

PUBLICATIONS

APS Abs 55–20739 (Feb. 14, 1980) Takemoto et al.
APS Ab 01–186815 (Jul. 26, 1989) Yamada.
APS Abs 56–113760 (Sep. 7, 1981) Onnishi et al.
Derwent Abs 89–052037 (J64003192) Watanabe.
APS Abs 62–158206 (Jul. 14, 1987) Svetsugu et al.
APS Abs 01–40412 (Feb. 10, 1989) Kamisaka et al.
APS Abs 01–132511 (May 25, 1989) Miyazaki.
APS Abs 58–41813 (Mar. 11, 1983) Awamura.

*Primary Examiner*—Herbert J. Lilling
*Attorney, Agent, or Firm*—Drucker & Sommers

[57] ABSTRACT

A composition of matter useful for enhancing the metabolism of the skin and mucosal tissue and thereby improving its health and appearance. The composition of matter has the furan (2)—R, wherein R is a straight $C_{9-36}$ alkyl chain, having the formula $CH_3-(CH_2)_n-(CH_2)_n CH_3$, (n=8 to 35). R can also be a straight unsaturated $C_{9-36}$ alkenyl chain with a single double bond, of the formula $-(CH_2)_n-CH=CH-(CH_2)_m-CH_3$, wherein n and m≠0 and n+m32 6 to 33. R can be a straight unsaturated $C_{9-36}$ chain, containing two to six double bonds, with the formula $CH_3-(CH_2)_m-(CH=CH)_x-(CH_2)_n-$, wherein m, x and n ≠0, m+2x+n=8 to 35. R can likewise be a straight unsaturated $C_{9-36}$ chain containing one to six double bonds and one triple bond, having the formula $CH_3-(CH_2)_m-C\equiv C-(CH=CH-CH_2)_x-$, wherein m and x≠0 and m+3x=6 to 33. R may be a straight unsaturated chain $C_{9-36}$ containing one to six double bonds and two to six triple bonds, having the structure $CH_3-(CH_2)_m-(C\equiv C-CH_2)_y-(CH=CH-CH_2)_x-(CH_2)_n-$, wherein m, y, x and n≠0 and m+3y+3x+n=8 to 35.

9 Claims, No Drawings

LIPIDIC FURANS USEFUL FOR SKIN THERAPEUTICS

BACKGROUND OF THE INVENTION

Field of the Invention

This invention relates to the field of lipidic furans, and more particularly to the use of certain lipidic furans characterized by an aliphatic hydrocarbon-chain with a minimum of nine carbon atoms, attached to the number two position on a furan ring, for improving the condition of human skin.

Description of Prior Art

For many years, there has been much folklore surrounding the beneficial qualities of avocados and avocado oil in improving the skin.

The Applicant observed that workers handling avocado oil have significantly moisturized, smoother appearing hands. The Applicant also observed a group of Central American Indians, whose diet included a high proportion of fresh avocados and avocados in a slightly warmed decoction, had significantly healthier looking skin than tribes in nearby areas that did not include avocado in their diets in significant proportions.

Some skin care specialists recommend placing packs of freshly mashed avocado pulp to the skin, as well as various preparations containing avocado and avocado oils to freshen and revitalize the skin and improve its appearance.

Over the years, there have been attempts to determine exactly what it is in the avocado which improves the appearance of the skin. However, these efforts have been unsuccessful.

In U.S. Pat. No. 4,386,067 to *Guillon*, the non-saponifiable fraction of avocado oil was mixed with the non-saponifiable fraction of soya-bean oil to form a mixture which aids in moisturizing the upper layer of skin. However, Guillon states that the composition of the non-saponifiable fraction is complex and is not completely known. No reference to lipidic furans is made.

U.S. Pat. No. 4,324,802 to Koulbanis et al. discloses that the non-saponifiable fractions of avocado oil and/or soy bean oil have useful dermatological properties for use in cosmetic compositions to improve the appearance of aging, dry or wrinkled skin. Again, however, the composition of the non-saponifiable fractions of the avocado oil is not identified.

In the journal article "New Compounds From Avocado Pear", by Y. Kashman, 1. Néeman and A. Liftshitz, Tetrahedron Vol. 25, pp. 4617–4631, compounds of Structure I, II and III with molecular weights 246, 248 and 250 were disclosed. No mention was made of the use of these compounds.

In the journal article "Partial Isolation Of and Characterization Of A New Natural Inhibitor Of Lysyl Oxidase From Avocado Seed Oil", by Mr. J. Werman, S. Mokady, and I. Néeman, J. Agric. Food Chem. 1990, 38, 2164–2168, it was reported that a unsaponifiable component ("C") of avocado seed oil inhibits the action of lysyl oxidase. Lysyl oxidase initiates cross-links in collagen and in collagenous connective tissue, including skin, and an over abundance of these crosslinks results in wrinkles, and a lack of elasticity in the skin. Werman et al. noted component "C" was derivable only from the unsaponifiable fraction of unrefined avocado oil or avocado seed oil. The researchers were unable to determine the composition of component "C", which was stated as being "probably a mixture of some polyalcoholic compounds, one of them having a molecular weight of 248 and being composed of a 17-carbon aliphatic chain with a furan ring." p. 2167.

In "The Avocatins—A New Class of Natural Products" by H. Magalhaes Alves, et al., An. Acad. brasil, Cieno, (1970), 42 (suplemento), compounds referred to as avocatins were discussed. These compounds are extractable from seeds of avocado pears, and have structures including the following alkyl furans:

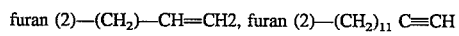

Each of these alkyl furans of the Alves, et al., article have a 13 carbon alkyl chain having one or two double bonds, or a single triple bond. The chain is attached to the number two position of a furan ring.

The short communication entitled "Isolation And Structure Elucidation of Growth Inhibitors For Silkworm Larvae From Avocado Leaves" by Ching-Fun Chang, et al., Agr. Biol. Chem., 39 (5), 1167–1168, 1975 discloses a growth inhibitor for Silkworm larvae, $C_{23}H_{C40}O_4$ which when treated with p-toluene sulfonic acid, yielded a new compound $C_{21}H_{34}O$, MW302, which is a two-substituted furan. The *Chang et al.* article fails to disclose the exact structure of this molecule or any cosmetic or therapeutic use of the compound for human skin use.

The journal article "A New Lipid Component Identified in Avocado Pear by GC-MS and NMR Spectroscopy", by N. Frega, et al. This journal article discloses the discovery of a new cyclic lipic compounds in the extracts of the unsaponifiable extracts of avocado having the following structure:

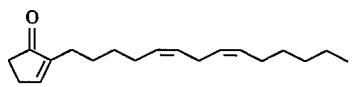

Not only is this compound not a furanyl lipid, but there was no discussion of for what these compounds might be useful.

Lastly, the article "Fatty Acids, Part XVI: The Synthesis Of All Isomeric $C_{18}$ Furan-Containing Fatty Acids", by M. S. F. Lie Ken Jie and C. H. Lam, Chemistry and Physics of Lipids 21 (1978) 275–287, discloses, as an intermediate in the synthesis of two and five substituted furanic compounds, the following structure:

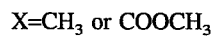

y=number of methylene groups

However, there is no discussion of what these compounds might be useful for.

Although a substantial amount of effort has been directed to elucidate what it is in avocados which make avocados good for the skin, these efforts have fallen short. No one in the past has identified the specific compounds from avocado which have useful cosmetic and therapeutic effects.

SUMMARY OF THE INVENTION

The invention is directed to a series of specific chemical compounds, termed lipidic furans, and their specificity to types I and III collagen, both of which are present in large amounts in the skin and mucosal tissues, (e.g. the tissue in the gums), and the use of these lipidic furans in enhancing the metabolic activities in these tissues. The enhanced metabolic activity exhibits itself by causing increases in the elasticity, protein content, DNA content, and for skin, increases in thickness of the epidermas and dermas. The enhanced metabolic activity is further exhibited by increases in the fibroblast population, total protein synthesis, collagen synthesis, heightened glucose metabolism in the treated tissues, and an overall improvement in the appearance and feel of the skin and mucosal tissue. These compounds are useful to combat dermal atrophy by slowing, and in many cases reversing the thinning skin, fine and coarse wrinkles, microvascular loss, capillary breakage and deformity brought about by chronological and photo aging of the skin. In sum, these compounds have the ability to markedly enhance the metabolism of skin and mucosal tissues.

The lipid furans of the invention have an aliphatic hydrocarbon with a minimum of nine carbon atoms attached to the number two position of the furan ring. These compounds have the general formula:

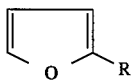

wherein R is a straight saturated chain alkyl $-(CH_2)_n CH_3$, and $n = 8$ to 35. R may also be a straight unsaturated alkyl chain $C_{9-36}$ with a single double bond, of the formula $-(CH_2)_n-CH=CH(CH-(CH_2)_m-CH_3$, n and $m \neq 0$ and $n+m=7$ to 34. R may also be a straight unsaturated $C_{9-36}$ chain, containing two to six double bonds, with the formula $CH_3-(CH_2)_m-(CH=CH)_x-(CH_2)_n-$, wherein m, x and $n \neq 0$, $m+2x+n=8$ to 35. R may also comprise a straight unsaturated $C_{9-36}$ chain containing one to six double bonds and one triple bond, having the formula $CH_3-(CH_2)_m-C\equiv C-(CH=CH-CH_2)_x-(CH_2)_n-$, wherein m, x and $n \neq 0$ and $m+3x+n=6$ to 36, or R may comprise a straight unsaturated chain $C_{9-36}$ containing one to six double bonds and two to six triple bonds, having the structure $CH_3-(CH_2)_m-(C\equiv C-CH_2)_y-(CH=CH-CH-CH_2)_x-)(CH_2)_n-$, wherein m, y, x and $n \neq 0$ and $m+3y+3x+n=8$ to 35.

Illustrative examples of compounds falling under the definition include the following:

Capric furan (2 Furanyl nonane)

Lauric furan (2 Furanyl hendecane)

Myristic furan (2 Furanyl tridecane)

Margaric furan (2 Furanyl hexadecane)

Arachidic furan (2 Furanyl nonadecane)

Lignoceric furan (2 Furanyl docosane)

Lauroleic furan (11-(2 Furanyl)-8-cis-hendecene)

Palmitoleic furan (15-(2 furanyl)-8-cis-pentadecene)

Cis-vaccenic furan (17-(2 furanyl)-10-cis-heptadecene)

Erucic furan (21-(2 furanyl)-12-cis-heneicosene)

Nervonic furan (23-(2 furanyl)-14-cis-trieicosene)

Linoleic furan (17-(2 furanyl)-8-11-cis-cis-heptadecadiene)

Arachidonic furan (19-(2 furanyl)-4-7-10-13-cis-cis-cis-cis-nonatetraene)

Crepenynic furan (18-(2 furanyl)-octadec-cis-8-en-11-yl)

Biological Activity

The compounds of the invention enhance the metabolism of the dermis of humans and animals and have therapeutic value when applied topically in a proper cosmetic control vehicle, or taken orally. For example, the control vehicle may comprise an oil-water, water-oil emulsions, or micro emulsion or micro encapsulated skin moisturizing formulation.

The Applicants have found that while all of the compounds listed above are useful, in particular the compound pictured below, 17-(2 Furanyl-8-11-cis-cis-heptadecadiene ("Linoleic Furan") has profound and beneficial effects on the epidermis and dermis of the skins and significantly the moisturization and smoothness of the skin.

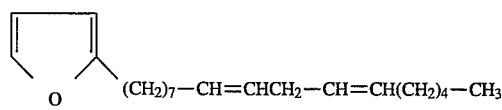

The Applicants have found that several beneficial therapeutic effects are caused by the use of Linoleic Furan as follows:

a) An increase in the number of cells in the skin as determined by DNA content and changes to the skin cells.

b) An increase in dermal and epidermal tissue as determined by protein content.

c) An increase in dermal metabolism as determined by $[^{14}C]$-glucose metabolism.

d) An increase in protein and collagen synthesis as determined by $[^3H]$-proline incorporation into protein and collagenase digestible protein.

e) An increase in dermal collagen content as determined by an increase in hydroxyproline.

f) An increase in the thickness of both the dermis and epidermis of skin treated with the Linoleic Furan in a suitable cosmetic formulation.

The above changes indicate that skin metabolism is "activated" by topical application of Linoleic Furan.

Empirical Experiments to Prove Structure of Linoleic Furan

Linoleic Furan can be extracted from the seed or pit of avocados, or can be synthesized, as is set forth in the companion patent application filed herewith by Jose De Hoyos Garcia, assigned to the same assignee. Linoleic Furan, which is either obtained by extraction from avocados, or produced synthetically, has a molecular weight of 302 Daltons, is oily, and has a light yellow color. Linoleic Furan was obtained from the avocado oil by separation. The separation scheme involved normal phase liquid chromatography on highly activated silica gel using hexane as the mobile phase. In this separation, 10 fractions were collected. Polarity was increased until the final fraction was removed by the use of 100% methanol. The separated fractions were subjected to mass spectroscopy. The major component of each fraction was determined by these analyses. Below are listed the results of these analyses. In addition to the materials listed in Table 1, 42 mg of material were insoluble in the original hexane solvent when 20.5 g of starting avocado seed extract were used.

TABLE 1

| FRACTION | MATERIAL (weight/weight) | % COMPOSITION |
| --- | --- | --- |
| A | Alkanes $C_{27}H_{56}$, $C_{29}H_{60}$, $C_{31}H_{64}$ | 6.1 |
| B–F | Alkenyl furans of the type | 62.0 |

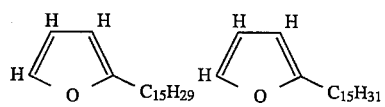

"B" = MW = 276    "C" = MW = 278

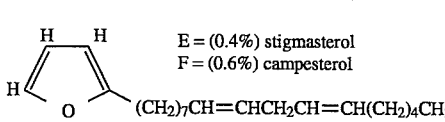

E = (0.4%) stigmasterol
F = (0.6%) campesterol

"D" = W = 302

| | | |
| --- | --- | --- |
| G | A mixture of F & H | 2.3 |
| H | Tocopherol | 8.3 |
| I | Sitosterol | 13.6 |
| J | - a tar like substance | 6.7 |

Upon testing these various fractions, it was found that Fraction D appeared to contain the most active material in terms of promoting dermal thickening (Table 2). This particular alkenyl furan containing fraction contained within it an alkenyl furan with a 302 Daltons molecular weight.

TABLE 2

EFFECT OF THE TOPICAL APPLICATION OF VARIOUS FRACTIONS OF AVOCADO SEED EXTRACT ON SKIN WEIGHT

| TREATMENT GROUP | PUNCH WEIGHT (mg wet weight/6 mm punch biopsy) |
| --- | --- |
| Control | 11.9 ± 0.1 |
| Control Vehicle | 11.7 ± 0.2 |
| Fraction A | 11.3 ± 0.4 |
| Fraction D | 13.0 ± 0.4*,** |
| Fraction F | 11.8 ± 0.3 |
| Fraction H | 11.0 ± 0.3 |
| Fraction J | 12.3 ± 0.4 |

Values represent the mean ± S.E.M. of 5 animals (S.E.M. = Standard Error of the Mean)
*Indicates significantly different from control at $p < 0.05$
**Indicates significantly different from vehicle control at $p < 0.05$.

In order to obtain more purified material with which subsequent work could be done, normal phase HPLC was initiated to separate Fraction D from the pit extract using preparative normal phase silica columns. With this system, a separation which gave three distinct peaks when monitored at 280 nm was achieved. In addition, thin layer plate chromatography also demonstrated that there was a separation of three distinct moieties. The three fractions which were obtained are: (1) a paraffin-like material, (2) a light yellow oil and (3) a dark yellow oil. The recovery of this material ranges from 40–55% of the applied material. The second step in the isolation is normal phase HPLC of the light yellow oil. A sufficient quantity of these three fractions was taken for additional purification. Using reverse phase HPLC on a C-18 column with an acetonitrile/tetrahydrofuran mobile phase, it was possible to divide the materials into families based on UV absorbance (Table 3).

Mass spectroscopy demonstrated that a separation of the 302 MW compound was achieved and that it eluted in the third fraction.

TABLE 3

| SOURCE OF MATERIAL | FRACTIONS OBTAINED | COMMENTS |
| --- | --- | --- |
| Normal Phase HPLC Fractions | | |
| #28–30 | A | max. absorbance at 266 nm |
| | B | colorless material which is greatest quantity (>80%) max. absorbance is <210 nm MW-302 |
| #9–10 | C | max. absorbance is at 266 nm |
| | D | max. absorbance is at 216 nm |
| #16 | E & J | max. absorbance is at 266 nm |
| | F, G, H & I | max. absorbance is at 216 nm |

Following these separations, it was found that the material B obtained by reverse phase chromatography accounted for better than 80% of the material in the fraction #28–30 from normal phase HPLC (Table 3). Thus, it appeared that this material was in the "dermal active material" and was the most prevalent molecular species in the dermal active material.

Although this work indicated that the alkenyl furan (MW 302) of fraction D of Table 2 was the molecule of interest, the precise structure of this compound was unknown. From the mass spectroscopy data and from the NMR data, it was evident that the structure contained two double bonds. Ozonolysis of the isolated compound was performed and mass spectroscopy and gas chromatography/mass spectroscopy on the oxidized fragments was carried out. This gave the structure D as presented in Table 1. However, this did not determine if the double bonds were "cis" or "trans".

To determine the absolute structure of the molecule, the $^1$H NMR spectrum in addition to the $^{13}$C NMR spectrum of the compound was examined. The $^1$H NMR spectrum in $CDCl_3$ is identical to the spectrum of linoleic acid (an all cis compound) for the common chemical groups with the exception of the α methylene to the carboxyl and the furan. Stronger evidence for a common double bond stereochemistry comes from the $^{13}$C NMR spectra. Trans double bonds would cause shifts of the α carbons up to 5 ppm in comparison to cis double bonds. The α carbons were assigned by heteronuclear correlation or decoupling and compared. The shifts were less than 0.1 ppm different which indicates that the double bonds have the same stereochemistry as in linoleic acid.

In addition, Raman spectroscopy on the purified 302 compound was performed. This study demonstrated a 1660 cm$^{-1}$ peak which corresponds well to what would be expected with a cis, cis configuration. From this, it was determined that the active fraction "D" is indeed Linoleic Furan.

Empirical Evidence of Biological Activity of Linoleic Furan

Experiments were conducted to demonstrate that Linoleic Furan increases skin protein synthesis and thereby increases skin tissue as determine by dermal DNA and protein content.

Four sets of 8 female hairless mice were treated each day for 14 days with 0.1 ml of each formulation. The formulations were as follows:

No treatment

Control Vehicle—oil-n-water emulsion

Vehicle with 3% (w/w), natural isolated Linoleic Furan

Vehicle with 3% (w/w) synthetic Linoleic Furan

In this and all subsequent studies, Linoleic Furan was formulated in an oil-in-water emulsion. The oil phase of this emulsion was 16% (w/w), the water phase ranged from 81–84% (w/w) and the concentration of Linoleic Furan ranged from 0–3% (w/w).

Skin composition and morphometric measurement were made as described in *The Effect of Retinyl Palmitate on Skin Composition and Morphometry*, , by Counts, D., Skreko, F., McBee, J. and Wich; Am. J. Soc. Cosmet. Chem. (1988) 39:235–240).

After treatment, the animals were sacrificed by cervical dislocation, the skin was removed and the subcutaneous tissue was dissected from the skin. A 6 mm punch biopsy was used to obtain a biopsy from the skin for analyses. For protein synthesis the biopsy was incubated in media containing [2,3-$^3$H] proline. Following 4 hours of incubation, the tissue was placed in 10% weight/volume (w/v) trichloroacetic acid and analyzed for incorporation of [2,3-$^3$H] proline into protein and collagenase digestible protein (Counts, D., Knighten, P. and Hegreberg, G., *Biochemical Changes in the Skin of Mink with Ehlers-Danlos Syndrome: Increased Collagen Biosynthesis in the Dermis of Affected Mink*. J. Invest. Dermatol. (1977) 9:521–526).

RESULTS

The analyses of the skin composition demonstrated that the addition of 3% of either natural or synthetic Linoleic Furan had the same effect on skin composition and weight (Table 4). Although all of the alkenyl furan containing formulations significantly increased protein synthesis, not all significantly increased collagen synthesis in this study (Table 5). Therefore, it is possible to use synthetically produced Linoleic Furan rather than isolated natural Linoleic Furan for skin treatment formulations.

The effect of Linoleic Furan on skin composition was confirmed by the change in skin morphometry as determined by microscopy (Table 6). Thus, topical application of Linoleic Furan causes an increase in skin thickness. These data suggest that treatment of skin on aging humans with Linoleic Furan may reverse the dermal atrophy known to be associated with human skin chronological and photo aging.

TABLE 4

EFFECT OF NATURAL AND SYNTHETIC LINOLEIC FURAN ON THE SKIN OF HAIRLESS MICE

| TREATMENT GROUP | PUNCH WEIGHT (mg/punch) | PROTEIN CONTENT (mg/punch) | DNA CONTENT (μg/punch) | COLLAGEN CONTENT (nmole HYP/Punch) |
|---|---|---|---|---|
| Control (no treatment) | 12.2 ± 0.7 (8) | 2.66 ± 0.19 (8) | 51.0 ± 7.8 (8) | 109 ± 29 (8) |
| Control Vehicle | 13.6 ± 0.4 (8) | 3.11 ± 0.25 (8) | 57.0 ± 2.7 (8) | 192 ± 28 (8) |
| 3% Natural Linoleic Furan | 18.1 ± 0.4*,** (8) | 4.52 ± 0.31*,** (8) | 96.7 ± 9.9*,** (8) | 185 ± 18* (8) |
| 3% Synthetic Linoleic Furan | 17.6 ± 0.4*,** (8) | 4.07 ± 0.3*,** (8) | 79.5 ± 3.7*,** (8) | 187 ± 26 (8) |

Values represent the mean ± S.E.M. of the number of animals in parentheses.
*Indicates significantly different from untreated control at $p < 0.05$.
**Indicates significantly different from the control vehicle treated group at $p < 0.05$.

TABLE 5

EFFECT OF NATURAL AND SYNTHETIC LINOLEIC FURAN ON SKIN PROTEIN AND COLLAGEN SYNTHESIS IN THE SKIN OF HAIRLESS MICE

| TREATMENT GROUP | TOTAL PROTEIN SYNTHESIS (DPM [$^3$H]-PRO/Punch) | COLLAGEN SYNTHESIS (DPM [$^3$H]-PRO/Punch) |
|---|---|---|
| Control (no treatment) | 3836 ± 597 (8) | 1895 ± 281 (8) |
| Control vehicle | 4145 ± 677 (8) | 1892 ± 351 (8) |
| 3% Natural Linoleic Furan | 6962 ± 1073*,** (7) | 2362 ± 517 (7) |
| 3% Synthetic Linoleic Furan | 6693 ± 790*,** (6) | 2561 ± 370 (6) |

Values represent the mean ± S.E.M. of the number of animals in parentheses.

*Indicates significantly different from untreated control at $p < 0.05$.
**Indicates significantly different from the control vehicle treated group at $p < 0.05$.

TABLE 6

EFFECT OF LINOLEIC FURAN OR SKIN MORPHOMETRY OF HAIRLESS MICE

| TREATMENT GROUP | EPIDERMAL THICKNESS | DERMAL THICKNESS (µm) | TOTAL THICKNESS |
|---|---|---|---|
| Control (no treatment) | 2.09 ± 0.07 (10) | 16.6 ± 1.3 (10) | 33.7 ± 1.5 (10) |
| Control vehicle | 5.69 ± 0.27* (10) | 22.1 ± 3.0 (10) | 39.5 ± 3.4 (10) |
| 3% Natural Linoleic Furan | 10.1 ± 0.55*,** (9) | 25.2 ± 1.7*,*** (9) | 46.1 ± 1.9* (9) |

Values represent the mean ± S.E.M. of the number of animals in parentheses.

*Indicates significantly different from untreated control at $p < 0.05$.
**Indicates significantly different from the control vehicle treated group at $p < 0.05$.

The Effect of Long Term Treatment With Linoleic Furan on Skin Metabolism and Morphometry

PURPOSE

To determine if the application of Linoleic Furan for extended periods of time gives the same results as the two weeks of treatment.

PROTOCOL

Female hairless mice were treated with 0.1 ml of either Control vehicle or 3% Linoleic Furan incorporated into Control vehicle each day for 6 weeks. At termination, the animals were biopsied for histology and skin biochemical analyses as described above.

RESULTS

As can be seen in Table 7, six weeks of treatment dramatically increased punch weight, protein content and DNA content in the skin. The increase in protein synthesis observed after 14 days of topical application Linoleic Furan was sustained after 6 weeks of application. In this study collagen synthesis was also increase (Table 8). The increase in epidermal, dermal and total skin thickness is also dramatically sustained (Table 9). Finally, while six weeks of treatment with control vehicle along increase (the number of fibroblasts within the dermis (Table 10), the addition of 3% Linoleic Furan to Control vehicle significantly increases the number of fibroblasts in the dermis over and above the increase due to Control vehicle along. Although treatment with Control vehicle also causes changes in all these parameters at 6 weeks, the effect is not as dramatic as the changes brought about by Control vehicle plus 3% Linoleic Furan. These increases in tissue can be partially explained by the increase in protein synthesis and the number of dermal cells (fibroblasts) in the skin of the treated groups (Tables 8 and 10).

TABLE 7

EFFECT OF LONG TERM TREATMENT (6 WEEKS) WITH LINOLEIC FURAN ON SKIN COMPOSITION OF HAIRLESS MICE

| TREATMENT GROUP | PUNCH WEIGHT (mg/punch) | PROTEIN CONTENT (mg/punch) | DNA CONTENT (µg/punch) | COLLAGEN CONTENT (nmole HYP/Punch) |
|---|---|---|---|---|
| Control (no treatment) | 10.9 ± 0.4 (10) | 0.94 ± 0.04 (10) | 40.4 ± 7.4 (10) | 211 ± 31 (10) |
| Control Vehicle | 13.6 ± 0.5* (9) | 1.40 ± 0.16* (9) | 47.1 ± 2.1* (9) | 202 ± 16 (9) |
| 3% Natural Linoleic Furan | 17.1 ± 0.4*,** (10) | 1.90 ± 0.05*,** (10) | 64.5 ± 2.7*,** (10) | 226 ± 15 (10) |

Values represent the mean ± S.E.M. of the number of animals in parenthesis.
*Indicates significantly different from untreated control at $p < 0.05$.
**Indicates significantly different from the control vehicle treated group at $p < 0.05$.

TABLE 8

EFFECT OF LONG TERM APPLICATION (6 WEEKS) OF LINOLEIC FURAN ON SKIN PROTEIN AND COLLAGEN SYNTHESIS OF HAIRLESS MICE

| TREATMENT GROUP | TOTAL PROTEIN SYNTHESIS | COLLAGEN SYNTHESIS |
|---|---|---|
| | (DPM[$^3$H]-PRO/Punch) | |
| Control (no treatment) | 4,750 ± 630 (10) | 2,830 ± 380 (10) |
| Control Vehicle | 5,900 ± 500 (9) | 3,210 ± 290 (9) |
| Vehicle + 3% natural Linoleic Furan | 10,100 ± 1360*,** (10) | 4,490 ± 620* (10) |

Values represent the mean ± S.E.M. of the number of animals of parenthesis.

*Indicates significantly different from untreated control at $p < 0.05$.
**Indicates significantly different from the control vehicle treated group at $p < 0.05$.

TABLE 9

EFFECT OF LONG TERM APPLICATION (6 WEEKS) OF LINOLEIC FURAN ON SKIN COMPOSITION OF HAIRLESS MICE

| TREATMENT GROUP | EPIDERMAL THICKNESS | DERMAL THICKNESS (μm) | TOTAL THICKNESS |
|---|---|---|---|
| Control (no treatment) | 2.10 ± 0.4 (10) | 18.1 ± 1.1 (10) | 32.7 ± 1.4 (10) |
| Control Vehicle | 5.86 ± 0.24 (10) | 19.4 ± 1.1 (10) | 36.6 ± 1.5 (10) |
| Vehicle + natural Linoleic Furan | 8.73 ± 0.69*,** (10) | 24.7 ± 0.8*,** (10) | 43.6 ± 0.9*,** (10) |

Values represent the mean ± S.E.M. of the number of animals in parenthesis.
*Indicates significantly different from untreated control at $p < 0.05$.
**Indicates significantly different from the control vehicle treated group at $p < 0.05$.

TABLE 10

EFFECT OF LONG TERM APPLICATION (6 WEEKS) OF LINOLEIC FURAN ON THE DERMAL FIBROBLAST POPULATION OF HAIRLESS MICE

| | FIBROBLAST POPULATION | |
|---|---|---|
| TREATMENT GROUP | (number of fibroblasts/ 0.274 mm surface) | (number of fibroblasts/mm$^2$ cross sectional area) |
| Control (no treatment) | 121 ± 9 (3) | 1637 ± 128 (3) |
| Control Vehicle | 242 ± 8* (3) | 2730 ± 173* (3) |
| Vehicle + 3% natural Linoleic Furan | 592 ± 54*,** (3) | 6174 ± 587*,** (3) |

Values represent the mean ± S.E.M. of the number of animals in parentheses.

*Indicates significantly different from untreated control at $p < 0.05$.
**Indicates significantly different from control vehicle treated group at $p < 0.05$.

Glucose Utilization In Skin After Treatment With Linoleic Furan

PURPOSE

Although there is an increase in general protein synthesis within skin treated with Linoleic Furan, it is not apparent where the extra energy necessary to support this increased activity is generated. An increase in aerobic glucose metabolism may account for a large portion of this energy. The Applicant determined that there is an increase in aerobic glucose metabolism.

ANIMAL TREATMENT PROTOCOL

Three groups containing 5 female hairless mice each were obtained. One group served as an untreated control group. The two remaining groups were treated with 0.1 ml of either vehicle or vehicle plus Linoleic Furan each day for 4 weeks. The treatment groups were as follows:
Control (untreated
Control vehicle
Vehicle+2% Linoleic Furan
Animals were sacrificed at the end of 4 weeks.

ASSAY PROTOCOL

After sacrifice, the skins were removed from the treated area of the animal and scraped free from the underlying tissues. A 6 mm diameter punch biopsy was next taken from the skin and placed in a test tube with ml of modified Krebs-Ringer solution (0.01M glucose) which had been aerated with $CO_2$: $O_2$ 5:95% to yield a pH of 7.3. Ten μCi of [U—$^{14}$C]glucose (ICN Biomedicals, Inc. 6.8 mCi/mmole) were added and the tube sealed and incubated for 45 minutes at 37° C. The reaction was stopped by the addition of 0.55 ml of 100% (w/v) trichloroacetic acid. The test tubes were incubated for an additional hour, and the released $^{14}CO_2$ was trapped on base impregnated paper and subsequently counted in a liquid scintillation counter.

RESULTS

Applicant found that treatment with Linoleic Furan significantly increased glucose metabolism (Table 11), and demonstrates that skin treated with Linoleic Furan has enhanced metabolic activity. As older skin is thought to be less efficient in glucose utilization than younger skin, the treatment with Linoleic Furan will be useful in treating aged skin.

TABLE 11

EFFECT OF TREATMENT WITH 2% LINOLEIC FURAN ON SKIN GLUCOSE UTILIZATION OR METABOLISM

| TREATMENT GROUP | GLUCOSE METABOLISM (DPM $^{14}CO_2$ formed/punch/45 min) |
|---|---|
| Control (untreated) | 1429 ± 628 (4) |
| Control vehicle | 1018 ± 182 (5) |
| Vehicle + 2% Linoleic Furan | 4042 ± 988** |

Values represent the mean ± S.E.M. of the number of animals in parentheses.

*Indicates significantly different from untreated control at $p < 0.05$.
**Indicates significantly different from the control vehicle treated group at $p < 0.05$.

The Effect of Increasing Doses of Linoleic Furan On Skin Composition An Protein Synthesis

EXPERIMENTAL PROTOCOL

Five sets of female hairless mice (10 mice per group) were either treated daily with 100 μl of a series of cosmetic formulations or used as untreated control animals. The treatment groups were as follows:

- Untreated Control
- Control vehicle
- Vehicle+1% (w/w) Natural Linoleic Furan
- Vehicle+2% (w/w) Natural Linoleic Furan
- Vehicle+3% (w/w) Natural Linoleic Furan The mice were treated for 15 days, sacrificed, and the skin taken for biochemical analysis, protein synthesis rate determination, and histology.

RESULTS

From these dose response studies, it was apparent that Linoleic Furan has a specific effect on skin thickness as determined in a variety of ways (skin thickness, punch biopsy weight, or punch biopsy composition). In addition, the DNA content (a measure of cellularity) was increased in each vehicle tested when compared to the vehicle control group (Tables 12, 13, and 14). These studies also indicated that there was an increase in the protein content due to the delivery of Linoleic Furan. Finally, in every treatment group there was a trend of increased total collagen content when compared to the control vehicle treated group (Table 12).

In addition to these findings, it was apparent that protein synthesis as well as collagen synthesis was increased by the addition of Linoleic Furan to the vehicle (Table 13). In addition, the biochemical findings were strongly supported by the finding that the skin thickness was increased in each of the test systems (both epidermis as well as dermis (Table 14)).

TABLE 13-continued

EFFECT OF INCREASING DOSES OF LINOLEIC FURAN ON SKIN PROTEIN AND COLLAGEN SYNTHESIS

| TREATMENT GROUP | TOTAL PROTEIN SYNTHESIS | COLLAGEN SYNTHESIS |
|---|---|---|
| | (DPM $^3$H-PRO/Punch) | |
| Linoleic Furan | (10) | (10) |
| Vehicle ± 3% | 5402 ± 724*,** | 1771 ± 248*,** |
| Linoleic Furan | (10) | (10) |

Values represent the mean ± S.E.M. of the number of animals in parentheses.

*Indicates significantly different from untreated control at $p < 0.05$.
**Indicates significantly different from the control vehicle treated group at $p < 0.05$.

TABLE 14

EFFECT OF INCREASING DOSES OF LINOLEIC FURAN ON SKIN MORPHOMETRY

| TREATMENT GROUP | EPIDERMAL THICKNESS (μm) | DERMAL THICKNESS (μm) | TOTAL THICKNESS (μm) |
|---|---|---|---|
| Control (no treatment) | 2.06 ± 0.03 (10) | 16.98 ± 1.03 (10) | 39.74 ± 1.19 (10) |
| Control Vehicle | 4.75 ± 0.15* (10) | 15.09 ± 1.10 (10) | 39.15 ± 1.45 (10) |
| Vehicle + 1% Linoleic Furan | 5.89 ± 0.35*,** (10) | 17.76 ± 0.89 (10) | 40.41 ± 1.60 (10) |
| Vehicle + 2% | 7.35 ± 0.6*,** | 20.22 ± | 41.31 ± 1.65 |

TABLE 12

EFFECT OF INCREASING DOSES OF LINOLEIC FURAN ON SKIN COMPOSITION

| TREATMENT GROUP | PUNCH WEIGHT (mg/punch) | PROTEIN CONTENT (mg/punch) | DNA CONTENT (μg/punch) | COLLAGEN CONTENT (nmole HYP/punch) |
|---|---|---|---|---|
| Control (no treatment) | 11.9 ± 0.4 (10) | 1.26 ± 0.08 (10) | 67.9 ± 4.6 (10) | 106 ± 12 (10) |
| Control vehicle | 13.9 ± 0.4 (10) | 1.83 ± 0.12* (10) | 55.6 ± 3.1* (10) | 146 ± 10* (10) |
| Vehicle + 1% Linoleic Furan | 14.6 ± 0.7* (10) | 2.08 ± 0.15* (10) | 69.2 ± 4.7** (10) | 160 ± 14* (10) |
| Vehicle + 2% Linoleic Furan | 16.1 ± 0.6*,** (10) | 2.07 ± 0.12* (10) | 74.7 ± 4.8** (10) | 184 ± 25* (10) |
| Vehicle + 3% Linoleic Furan | 17.8 ± 0.6*,** (10) | 2.51 ± 0.51*,** (9) | 84.2 ± 4.1*,** (9) | 173 ± 12* (9) |

Values represent the mean ± S.E.M. of the number of animals in parentheses.
*Indicates significantly different from untreated control at $p > 0.05$.
**Indicates significantly different from the control vehicle treated group at $p < 0.05$.

TABLE 13

EFFECT OF INCREASING DOSES OF LINOLEIC FURAN ON SKIN PROTEIN AND COLLAGEN SYNTHESIS

| TREATMENT GROUP | TOTAL PROTEIN SYNTHESIS | COLLAGEN SYNTHESIS |
|---|---|---|
| | (DPM $^3$H-PRO/Punch) | |
| Control (no treatment) | 1582 ± 75 (9) | 960 ± 35 (9) |
| Control Vehicle | 3684 ± 239* (10) | 1350 ± 90* (10) |
| Vehicle ± 1% Linoleic Furan | 3974 ± 462* (10) | 1485 ± 157* (10) |
| Vehicle ± 2% | 4623 ± 556* | 1780 ± 232*,** |

TABLE 14-continued

EFFECT OF INCREASING DOSES OF LINOLEIC FURAN ON SKIN MORPHOMETRY

| TREATMENT GROUP | EPIDERMAL THICKNESS (μm) | DERMAL THICKNESS (μm) | TOTAL THICKNESS (μm) |
|---|---|---|---|
| Linoleic Furan | (10) | 1.08*,** (10) | (10) |
| Vehicle + 3% Linoleic Furan | 9.11 ± 0.0.50*,** (10) | 20.74 ± 1.90** (10) | 42.58 ± 1.55 (10) |

Values represent the mean ± S.E.M. of the number of animals in parentheses.

TABLE 14-continued

EFFECT OF INCREASING DOSES OF LINOLEIC FURAN
ON SKIN MORPHOMETRY

| TREATMENT GROUP | EPIDERMAL THICKNESS ($\mu m$) | DERMAL THICKNESS ($\mu m$) | TOTAL THICKNESS ($\mu m$) |
| --- | --- | --- | --- |

*Indicates significantly different from untreated control at $p < 0.05$.
**Indicates significantly different from the control vehicle treated group at $p < 0.05$.

I claim:

1. A method for enhancing the metabolism of skin and mucosal tissue and thereby improving its health and appearance, comprising the step of administering a pharmacologically effective amount of lipidic furans to a person, said lipidic furans having the following general formula:

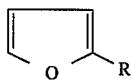

wherein R is selected from the group consisting of one of a straight $C_{9-36}$ alkyl chain, having the formula $-(CH_2)_n CH_3$, wherein $n=8$ to 35; a straight unsaturated alkenyl $C_{9-36}$ chain with a single double bond, of the formula $-(CH_2)_n-CH=CH-(CH_2)_m-CH_3$, wherein n and $m \neq 0$ and $n+m=7$ to 34, a straight unsaturated $C_{9-36}$ chain, containing two to six double bonds, with the formula $CH_3-(CH_2)_m-(CH=CH)_x-(CH_2)_n-$, wherein m, x and $n \neq 0$, and $m+2x+n=8$ to 35; a straight unsaturated chain, having the formula $-(CH_2)_7CH=CH-CH_2-CH=CH(CH_2)_4-CH_3$; a straight unsaturated $C_{9-36}$ chain containing one to six double bonds and one triple bond, having the formula $CH_3-(CH_2)_m-C\equiv C-(CH=CH-Ch_2)_x-(CH_2)_n-$, wherein m, x and $n \neq 0$ and $m+3x+n=6$ to 33, a straight unsaturated chain $C_{9-36}$ containing one to six double bonds and two to six triple bonds, having the structure $CH_3-(CH_2)_m-(C\equiv C-CH_2)_y-(CH=CH-CH_2)_x-(CH_2)_n-$, wherein m, y, x and $n \neq 0$ and $m+3y+3x+n=8$ to 35.

2. The method of claim 1, wherein R is $-(CH_2)_7CH=CH-CH_2-CH=CH(CH_2)_4-CH_3$, and all double bonds are cis.

3. The method of claim 1, wherein said lipidic furans are topically applied to the skin in an appropriate carrier vehicle.

4. The method of claim 1, wherein said lipidic furan are taken orally.

5. The composition of matter of claim 1, wherein said lipidic furan is at a concentration range of approximately 1 to 3%.

6. A method for enhancing the metabolism of skin and mucosal tissue and thereby improving its health and appearance, comprising the step of administering a pharmacologically effective amount of a lipidic furan to a person, said lipidic furans having the following formula:

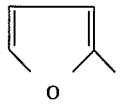 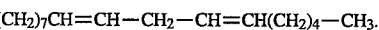

7. The method of claim 6, wherein said lipidic furan is topically applied to the skin in an appropriate carrier vehicle.

8. The method of claim 6, wherein said lipidic furan is taken orally.

9. The composition of matter of claim 7, wherein said lipidic furan is applied at a concentration range of approximately 1 to 3% in a carrier vehicle.

* * * * *